United States Patent [19]

Grassmé

[11] 4,063,099

[45] Dec. 13, 1977

[54] DENTAL APPARATUS FOR X-RAY DIAGNOSIS

[75] Inventor: Ulrich Grassmé, Nurnberg, Germany

[73] Assignee: Siemens Aktiengesellschaft, Berlin & Munich, Germany

[21] Appl. No.: 679,501

[22] Filed: Apr. 22, 1976

[30] Foreign Application Priority Data

Apr. 25, 1975 Germany .............................. 2518549

[51] Int. Cl.$^2$ .............................................. H05G 1/30
[52] U.S. Cl. ..................................... 250/413; 250/402
[58] Field of Search ................ 250/439 P, 444, 445 T, 250/322, 402, 413, 415, 491

[56] References Cited

U.S. PATENT DOCUMENTS

| 2,942,114 | 7/1960 | McNally | 250/413 |
|---|---|---|---|
| 3,737,660 | 6/1973 | Ando et al. | 250/439 P |
| 3,743,832 | 7/1973 | Wright | 250/439 P |
| 3,894,235 | 7/1975 | Franke | 250/402 |

*Primary Examiner*—Bruce C. Anderson
*Attorney, Agent, or Firm*—Hill, Gross, Simpson, Van Santen, Steadman, Chiara & Simpson

[57] ABSTRACT

A dental apparatus for x-ray diagnosis comprises a unit, which includes an x-ray tube and a film holder and is adapted to rotate around a vertical axis, and a support for the head of a patient disposed between the x-ray tube and the film carrier. The apparatus produces general tomograms with a radiographic recording time which is predetermined by a timer mechanism of the x-ray tube/film carrier unit, and by at least one further recording value which is adjustable by a regulating device to provide a nominal or reference recording value. The unit further comprises an x-ray detector disposed on the film carrier in a position in which the detector receives at least the x-ray radiation penetrating the jaw of the patient during the entire duration of an x-ray recording, during which period the detector supplies an electrical signal corresponding to the x-ray dose output. The detector and the regulating device are connected to an x-ray dose output regulator so as to provide automatic exposure such that the adjustable recording value is related to the output signal of the x-ray detector, whereby the x-ray dose output is adapted to a desired value resulting in an optimal exposure of the film. The regulating device for the nominal value for the output dose regulator is associated with a transmitter for transmitting an electrical signal related to the speed of transport of the film such that the nominal value is adjusted to be a function of the transport speed of the film.

5 Claims, 3 Drawing Figures

DENTAL APPARATUS FOR X-RAY DIAGNOSIS

FIELD OF THE INVENTION

The invention relates to dental apparatus for x-ray diagnosis and particularly to means for obtaining automatic optimum exposure of x-ray film.

BACKGROUND OF THE INVENTION

It is possible by means of dental apparatus for x-ray diagnosis as described in U.S. patent application Ser. No. 618,514 filed Jan. 10, 1975 to produce general tooth and jaw x-ray pictures while automatically controlling the x-ray dose output received by the film in accordance with a preset nominal value, so that an x-ray picture is produced with automatic exposure. However, the darkening or image formation on the film depends not only on the x-ray dose output of the radiation acting on the film, but also on the speed at which the x-ray film is transported. Therefore, the apparatus for dental x-ray diagnosis according to the aforesaid Application produces x-ray pictures with optimal darkening of the picture only if the rate of film transport is constant. However, it has been found in practice that variations or fluctuations of said transport speed of the film do occur.

SUMMARY OF THE INVENTION

It is an object of the present invention to provide a refinement for a unit for x-ray diagnosis of the aforementioned type such that x-ray pictures with a faultless darkening can be achieved even though variations of the film transport speed may occur.

According to the present invention, this object is achieved by associating the nominal value transmitter of the x-ray dose output regulator with a transmitter for sending an electric signal that corresponds with the rate of film transport, and furthermore with an adjusting member which is controlled by said signal for adjusting the value desired for the x-ray dose output as a function of the rate of film transport.

In the dental unit for x-ray diagnosis according to the present invention, the nominal or desired value of the x-ray dose output supplied to the film depends on the film transport speed. This dependency is selected in such a manner that in spite of fluctuations of said film transport speed, x-ray pictures are achieved which are optimally darkened in all reas.

Further details and advantages of the present invention will be evident from the following description of one embodiment with reference to the appended drawings.

DETAILED DESCRIPTION OF THE DRAWINGS

Figure 1:
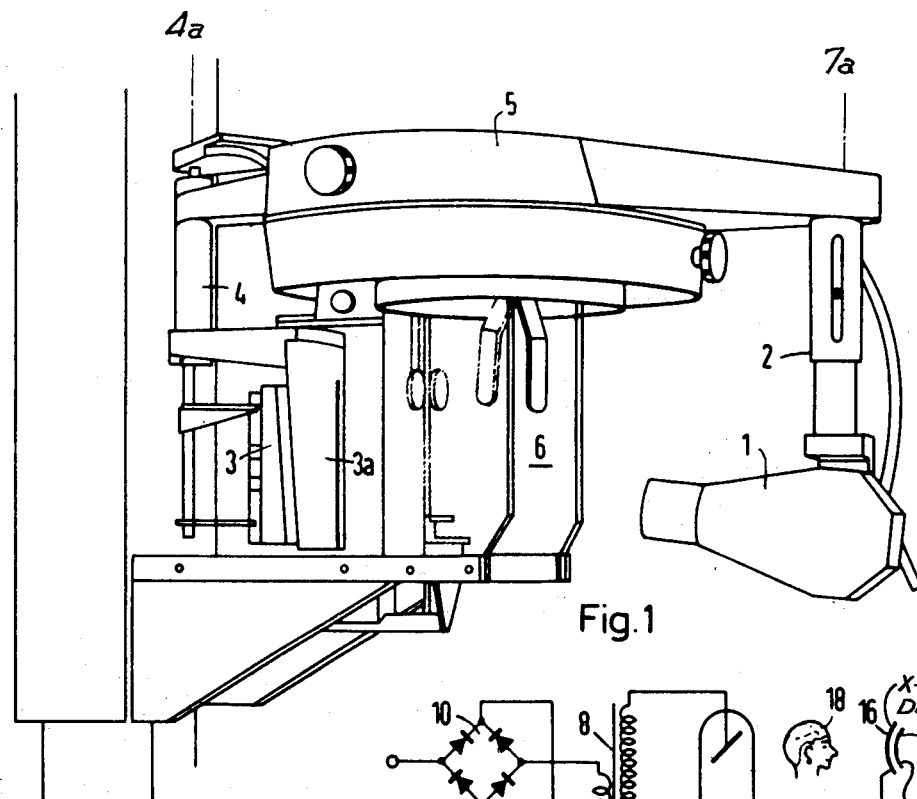
FIG. 1 is a diagrammatic illustration of a dental unit for x-ray diagnosis according to the present invention.

The apparatus for dental x-ray diagnosis according to FIG. 1 comprises a housing 1 containing an x-ray tube 7, the housing being vertically adjustable on a carrier 2. X-ray film 17 (FIGS. 2 and 3) is contained in a semi-circular cassette which is secured on a cassette holder 3. The cassette holder 3 is attached to a carrier 4. Carriers 2 and 4 are mounted on a support device 5. A support 6 for the head of a patient is disposed between cassette holder 3 and housing 1. Viewed in the direction of the x-rays, a slit shutter 3a is arranged in front of cassette holder 3.

Figure 3:
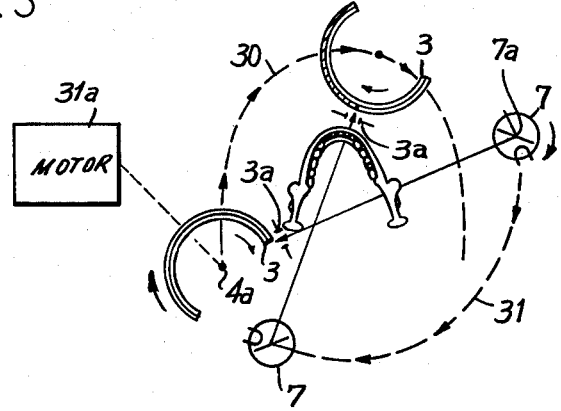
FIG. 3 is a diagrammatic plan view showing the travel of the film and x-ray tube of the dental unit in the course of producing an x-ray picture.

For producing a general x-ray picture of a tooth or the jaw, the head of the patient is supported in head support 6. In the course of picture taking, the x-ray tube housing 1 with the x-ray tube and cassette holder 3 with the x-ray film move around the head of the patient, during which operation both the x-ray tube housing 1 and cassette holder 3 are turned around respective vertical axes 7a and 4a in such a manner that the x-rays strike the teeth at right angles, while the spacing between the row of teeth and the x-ray film remains constant. During the movement of cassette holder 3 and x-ray tube housing 1 around the head of the patient, the teeth are successively photographed and images thereof are formed over the length of the film, which also includes of course, an image of the jaw. In said movement, the rotary axis 4a of the cassette holder 3 is the same as the axis of carrier 4. A motor 31a (diagrammatically shown in FIG. 3) is arranged in the support device 5 for effecting said rotary movement of the cassette holder 3 around the axis 4a whereby the film is continuously transported in front of the shutter and exposed as diagrammatically shown in FIG. 3 in which the exposed portion of the film is cross-hatched. FIG. 3 shows the travel of holder 3 along its path of revolution 30 around holder 6 while housing 1 with x-ray tube 7 travels along path of revolution 31. The holder 3 also rotates around axis 4a under the drive of motor 31a. An uninterrupted continuous radiograph is uniformly produced on the film in the course of the revolving movement of the housing 1 and the cassettes holder 3 around support 6 while the holder 3 and housing 1 undergo respective turning around their respective axes. Up to this point the construction is the same as that in application Ser. No. 618,614.

Figure 2:
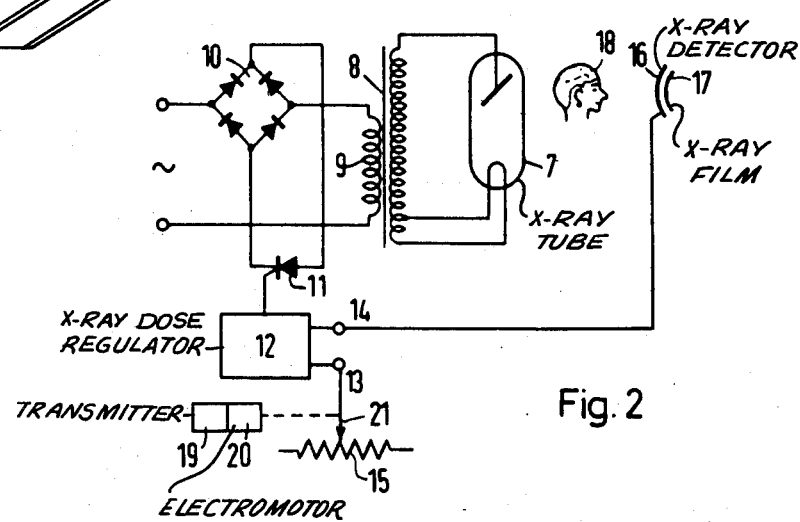
FIG. 2 is a circuit diagram of part of the unit of FIG. 1.

FIG. 2 shows the x-ray tube 7 disposed in housing 1. The x-ray tube 7 is supplied with high voltage and filament voltage by the secondary winding of a high voltage transformer 8. The primary winding 9 of high voltage transformer 8 is connectable to the power supply through a diode bridge 10 with, a thyristor 11 being connected in the DC-branch of the diode bridge. The thyristor 11 receives ignition pulses from an x-ray dose output regulator 12 having a nominal value or reference value input 13 and an actual value input 14. The nominal value or reference value signal is obtained from a nominal value or reference value transmitter 15, whereas the actual value signal of the x-ray dose output is supplied by an x-ray detector 16. The x-ray detector 16 is disposed in front of x-ray film 17 supported on film carrier 3. The head 18 of the patient rests between the x-ray tube 7 and x-ray film 17.

The x-ray dose regulator 12 receives at input 13 a signal which for a pre-determined recording time of, for example, 15 seconds (which time takes into account the transport time of the recording unit, namely of cassette holder 3 and x-ray tube housing 1) results in an optimal darkening or imaging of the film. In response to a difference between the nominal value signal at input 13 and the actual value signal at input 14, regulator 12 adjusts the application of ignition pulses to thyristor 11 in such a way that the x-ray dose output is maintained at a constant pre-determined value.

Based on the presently used recording principle, the speed of transport of the cassette holder 3 around its support axis 4a and thus also the speed of transport of the x-ray film can change. For this reason a transmitter is arranged in support device 5 for transmitting electrical signal which corresponds to the speed of transport of cassette holder 3, and thus to the speed of transport of the x-ray film. This transmitter is designated by reference numeral 19 in FIG. 2. This transmitter may be a tachogenerator connected in support device 5 to a shaft which drives carrier 4 around its axis. Connected to transmitter 19 is an adjusting device 20, for example, an electromotor, which adjusts the tap 21 of the nominal value transmitter 15 as a function of the signal from transmitter 19. Tap 21 is also adjustable by hand for adjusting the nominal value of the x-ray dose output to the sensitivity of the x-ray film.

In the apparatus for x-ray diagnosing described in the foregoing, the adjusted or preset nominal or reference value for the dose output is varied as a function of fluctuations of the speed of transport of the film in such manner that the darkening or exposure of the x-ray film remains constant in spite of fluctuations of speed of transport of the film. Therefore, recordings with an optimum darkening are achieved in all cases.

What is claimed is:

1. In an apparatus for x-ray diagnosis comprising a unit rotatable about a vertical axis and having an x-ray tube and an opposed holder for x-ray film, a support for the head of a patient disposed between said x-ray tube and said holder, shutter means disposed in front of said holder for passage of x-rays to said film for producing tomograms, x-ray detector means disposed in a position for receiving at least the x-ray radiation passing through the jaw of a patient during the entire duration of a recording and for providing an electrical signal corresponding to the actual x-ray dose output, adjustable means for producing a reference electrical signal corresponding to the desired exposure time for the x-ray film, energizing means for said x-ray tube, and an x-ray dose regulator means having a first input for receiving the electrical signal from the detector means and a second input for receiving the reference electrical signal, said regulator means activating the energizing means to regulate the x-ray dose output supplied to the film to provide an optimum exposure thereof in response to a comparison of the actual x-ray dose output to the reference electrical signal, the improvements comprising means for producing an output signal related to the speed of transport of the holder and film, and means for receiving said output signal and adjusting the reference electrical signal of said adjustable means in relation thereto so that the reference signal for a desired value x-ray dose output is adjusted as a function of the speed of transport of the holder and film in addition to its dependent on the exposure time of the film.

2. In an apparatus according to claim 1, wherein said means for producing the output signal related to the speed of transport of the holder and film comprises a tachogenerator.

3. In an apparatus according to claim 2, wherein said means for regulating the reference electrical signal comprises an electromotor coupled to said tachogenerator.

4. In an apparatus according to claim 3, wherein said adjustable means comprises a reference signal transmitter with an adjustable tap, said electromotor being coupled to said adjustable tap to vary its position in response to the output signal of the tachogenerator.

5. In an apparatus according to claim 4, wherein said tap is manually adjustable for regulating the reference value of the x-ray dose output to the sensitivity of the x-ray film.

* * * * *